United States Patent
Kerkhoffs et al.

(10) Patent No.: US 10,342,905 B2
(45) Date of Patent: Jul. 9, 2019

(54) BLOOD FLOW SYSTEM WITH VARIABLE SPEED CONTROL

(71) Applicant: CircuLite, Inc., Teaneck, NJ (US)

(72) Inventors: Wolfgang Kerkhoffs, Aachen (DE); Oliver Marseille, Aachen (DE); Michael Martin, Wurselen (DE); Robert C. Farnan, Ridgewood, NJ (US); John P. Budris, Cheshire, CT (US); J. Christopher Flaherty, Auburndale, FL (US)

(73) Assignee: CircuLite, Inc., Teaneck, NJ (US)

( * ) Notice: Subject to any disclaimer, the term of this patent is extended or adjusted under 35 U.S.C. 154(b) by 604 days.

(21) Appl. No.: 14/017,505

(22) Filed: Sep. 4, 2013

(65) Prior Publication Data

US 2014/0073837 A1    Mar. 13, 2014

Related U.S. Application Data

(60) Provisional application No. 61/700,518, filed on Sep. 13, 2012.

(51) Int. Cl.
*A61M 1/10* (2006.01)
*A61M 1/12* (2006.01)

(52) U.S. Cl.
CPC ........... *A61M 1/1086* (2013.01); *A61M 1/101* (2013.01); *A61M 1/1008* (2014.02); *A61M 1/1029* (2014.02); *A61M 1/122* (2014.02); *A61M 2205/3334* (2013.01)

(58) Field of Classification Search
None
See application file for complete search history.

(56) References Cited

U.S. PATENT DOCUMENTS

| | | | |
|---|---|---|---|
| 4,662,358 A | 5/1987 | Farrar et al. | |
| 4,688,998 A | 8/1987 | Olsen et al. | |
| 5,267,940 A | 12/1993 | Moulder | |
| 5,352,180 A | 10/1994 | Candelon et al. | |
| 5,676,162 A | 10/1997 | Larson, Jr. et al. | |
| 5,820,542 A | 10/1998 | Dobak, III et al. | |
| 5,888,242 A | 3/1999 | Antaki et al. | |
| 5,965,089 A * | 10/1999 | Jarvik et al. | 422/44 |
| 6,042,532 A * | 3/2000 | Freed et al. | 600/18 |
| 6,066,086 A | 5/2000 | Antaki et al. | |

(Continued)

FOREIGN PATENT DOCUMENTS

| WO | 2012078873 A1 | 6/2012 |
|---|---|---|
| WO | 2014107424 A2 | 7/2014 |

OTHER PUBLICATIONS

U.S. Patent and Trademark Office, Invitation to Pay Additional Fees in PCT Application No. PCT/US13/57986, dated Jan. 23, 2014.

(Continued)

*Primary Examiner* — Erica S Lee
(74) *Attorney, Agent, or Firm* — Christopher & Weisberg, P.A.

(57) ABSTRACT

A fluid flow system for a patient is disclosed. A fluid drive module includes a fluid drive element, a housing, and a chamber located between the housing and the fluid drive element. A controller or control module modifies the speed of the fluid drive element during use, such as to prevent thrombus or otherwise improve flow conditions. Methods of alternating fluid flow are also provided.

5 Claims, 6 Drawing Sheets

(56) References Cited

U.S. PATENT DOCUMENTS

| | | | |
|---|---|---|---|
| 6,116,862 | A | 9/2000 | Rau et al. |
| 6,176,848 | B1 | 1/2001 | Rau et al. |
| 6,387,323 | B1 | 5/2002 | Afzal et al. |
| 6,527,699 | B1 | 3/2003 | Goldowsky |
| 6,540,658 | B1 | 4/2003 | Fasciano et al. |
| 6,610,004 | B2 | 8/2003 | Viole et al. |
| 6,783,328 | B2 | 8/2004 | Lucke et al. |
| 6,991,595 | B2 | 1/2006 | Burke et al. |
| 7,591,777 | B2 | 9/2009 | LaRose |
| 7,645,225 | B2 | 1/2010 | Medvedev et al. |
| 7,742,821 | B1 | 6/2010 | Vamos et al. |
| 7,850,594 | B2 | 12/2010 | Sutton et al. |
| 7,862,501 | B2 | 1/2011 | Woodard |
| 7,963,905 | B2 | 6/2011 | Salmonsen et al. |
| 7,988,728 | B2 | 8/2011 | Ayre |
| 8,096,935 | B2 | 1/2012 | Sutton et al. |
| 8,226,712 | B1 | 7/2012 | Frazier et al. |
| 2003/0045772 | A1* | 3/2003 | Reich et al. ............. 600/18 |
| 2003/0074144 | A1 | 4/2003 | Freed et al. |
| 2005/0071001 | A1* | 3/2005 | Jarvik ................ 623/3.28 |
| 2005/0215843 | A1 | 9/2005 | Medvedev |
| 2006/0074465 | A1 | 4/2006 | Webb |
| 2007/0073393 | A1* | 3/2007 | Kung et al. ............ 623/3.13 |
| 2007/0276480 | A1 | 11/2007 | Tansley et al. |
| 2008/0261597 | A1* | 10/2008 | Hayama ............. H04W 36/30 455/436 |
| 2009/0138080 | A1 | 5/2009 | Siess et al. |
| 2010/0168848 | A1 | 7/2010 | Horvath et al. |
| 2011/0015693 | A1 | 1/2011 | Williamson |
| 2012/0078030 | A1 | 3/2012 | Bourque |
| 2012/0150291 | A1 | 6/2012 | Aber et al. |
| 2012/0172657 | A1 | 7/2012 | Marseille et al. |

OTHER PUBLICATIONS

European Patent Office, International Search Report and Written Opinion in PCT Application Serial No. PCT/US14/049393, dated Oct. 31, 2014.
U.S. Patent and Trademark Office, Internatinoal Search Report and Written Opinion in PCT Application No. PCT/US13/57986, dated Apr. 9, 2014.
The International Bureau of WIPO, International Preliminary Report on Patentability in PCT Application No. PCT/US13/57986, dated Mar. 26, 2015.
European Patent Office, Supplementary European Search Report in EP Application Serial No. 13838004, dated Jul. 29, 2016.

* cited by examiner

BLOOD FLOW SYSTEM WITH VARIABLE SPEED CONTROL

CROSS-REFERENCE TO RELATED APPLICATIONS

This application claims the benefit of U.S. Provisional Patent Application Ser. No. 61/700,518, filed on Sep. 13, 2012, the disclosure of which is incorporated by reference herein, in its entirety.

This application is also related to U.S. patent application Ser. No. 12/392,623, entitled "Devices, Methods and Systems for Establishing Supplemental Blood Flow in the Circulatory System", filed Feb. 25, 2009 (pending); U.S. patent application Ser. No. 13/025,757, entitled "Devices, Methods and Systems for Establishing Supplemental Blood Flow in the Circulatory System", filed Feb. 11, 2011 (pending); U.S. patent application Ser. No. 12/396,048, entitled "Intravascular Blood Pump and Catheter", filed Mar. 2, 2009 (pending); U.S. patent application Ser. No. 13/017,205, entitled "Test Controller for a Rotary Pump", filed Jan. 31, 2011 (pending); U.S. patent application Ser. No. 11/084,452, entitled "Pump", filed Mar. 18, 2005 (now U.S. Pat. No. 8,512,012); U.S. patent Ser. No. 09/202,538, entitled "Blood Pump", filed Dec. 16, 1998 (now U.S. Pat. No. 6,116,862); U.S. patent Ser. No. 09/155,818, entitled "Intravascular Blood Pump", filed Oct. 5, 1998 (now U.S. Pat. No. 6,176,848); each of which is incorporated herein by reference in their entirety.

FIELD OF THE INVENTION

The present invention relates generally to medical devices, systems and methods, and more particularly, to device and methods for assisting in the conduction of bodily fluids such as blood.

BACKGROUND OF THE INVENTION

Various devices, systems and methods have been utilized to assist in conducting bodily fluids. For instance, blood pumps with inflow and outflow cannulae assist the heart in circulating blood in a patient experiencing congestive heart failure, and a transplant organ has either not been located or the patient is not a suitable candidate for the transplant. Accordingly, the blood pump can be fluidically attached to the left side of the heart and then located remotely, such as subcutaneously or submuscularly in a manner similar to a pacemaker, in what is referred to as a "pump pocket." The pump pocket can be generally located at a position that is accessible by a surgical incision from below the collarbone, over the pectoral muscle, and toward the breast. A cannula can then be used to fluidically couple the heart to the pump. In still another example, a cannula is inserted into the bladder or kidney, such as in dialysis or to treat urinary obstruction or infection.

A fluid drive module, such as a pump, can be used to circulate the bodily fluid. Areas of insufficient flow, such as low-flow areas within or proximate to the fluid drive module, can result in the circulated fluid undesirably transitioning to solid matter. With blood pumping systems, blood in a stasis or near-stasis condition can transition to thrombus. Creation of thrombus or other solid matter can result in reduced flow of the fluid drive module or, more significantly, release of solid matter into the patient such as a released embolus that causes a stroke, heart attack, or other ischemic event.

For these and other reasons, there is a need for devices, systems and methods which reduce the likelihood of inadequate flow conditions and creation of emboli. Desirably, the systems, methods and devices will improve long term efficacy and minimize device complications.

SUMMARY

Embodiments of the present inventive concepts may be directed toward blood and other fluid flow systems for a patient, as well as methods for providing circulating fluid for a patient. Fluid and/or blood flow systems can include fluid and/or blood circulation systems or fluid and/or blood delivery systems.

According to one aspect of the present inventive concepts, a blood flow system for a patient includes a control module and a fluid drive module including a fluid drive element; a housing surrounding the fluid drive element; and a chamber located between the housing and the fluid drive element. The control module operates the fluid drive module at a first speed for a first time period, where the first speed generates a first speed flow pattern comprising multiple first speed flow vectors and further operates the fluid drive module at a second speed for a second time period, where the second speed is constructed and arranged to modify one or more of the multiple first speed flow vectors.

The system can be constructed and arranged to reduce thrombus formation.

The system can be constructed and arranged to perform a function selected from the group consisting of: reducing cell adhesion; preventing cell adhesion; reducing protein adhesion; preventing protein adhesion; reducing cellular aggregation; preventing cellular aggregation; reducing a nidus for thrombus formation; eliminating a nidus of thrombus formation; reducing one or more eddy currents; preventing one or more eddy currents; reducing a zone of stagnant flow; preventing a zone of stagnant flow; reducing a steady state flow; preventing a steady state flow; enhancing volume loading of an atrium of the heart; allowing volume loading of an atrium of the heart; and combinations of these.

The modified one or more multiple first speed flow vectors can comprise one or more first speed flow vectors positioned in the chamber. Additionally or alternatively, the modified one or more multiple first speed flow vectors can comprise one or more first speed flow vectors positioned outside the chamber, for example positioned in a cannula in fluid communication with the chamber, positioned in a chamber of the heart of the patient, and/or positioned in the artery of the patient.

The second speed can be constructed and arranged to modify the flow rate and/or the direction of one or more of the multiple first speed flow vectors.

The control module can further operate the fluid drive module at a third speed for a third time period, for example where the third speed can be constructed and arranged to modify one or more of the multiple first speed flow vectors. The second speed can generate a second speed flow pattern comprising multiple second speed flow vectors, and the third speed can be constructed and arranged to modify one or more of the multiple second speed flow vectors. The second speed can be greater than the first speed and the third speed can be less than the first speed.

The control module can be constructed and arranged to allow an operator to set the first speed between a minimum speed and a maximum speed. The second speed can comprise the minimum speed, and the control module further can operate the fluid drive module at a third speed for a third time period, where the third speed can comprise the maximum speed. Conversely, the second speed can comprise the maximum speed, and the control module further can operate the fluid drive module at a third speed for a third time period, where the third speed can comprise the minimum speed.

The first speed can comprise a rotational velocity greater than 100 rpm. The first speed can comprise a rotational velocity between 100 rpm and 100,000 rpm. The first speed can comprise a rotational velocity between 5,000 rpm and 50,000 rpm. The first speed can comprise a rotational velocity between approximately 20,000 rpm and 28,000 rpm, such as a rotational velocity between approximately 21,000 rpm and 27,000 rpm, and the second speed can comprise a rotational velocity of approximately 28,000 rpm, or approximately 20,000 rpm.

The second speed can comprise a rotational velocity that is 1% to 100% greater than a rotational velocity of the first speed. The second speed can comprise a rotational velocity that is 5% to 75% greater than a rotational velocity of the first speed. The second speed can comprise a rotational velocity that is 10% to 50% greater than a rotational velocity of the first speed. The second speed can comprise a rotational velocity that is up to 40% greater than a rotational velocity of the first speed.

The second speed can comprise a rotational velocity that is 1% to 99% of a rotational velocity of the first speed. The second speed can comprise a rotational velocity that is 25% to 95% of a rotational velocity of the first speed. The second speed can comprise a rotational velocity that is 50% to 90% of a rotational velocity of the first speed. The second speed can comprise a rotational velocity that is 60% to 99% of a rotational velocity of the first speed.

The first time period can comprise a period between 1 second and 1 hour. In some embodiments, the first time period can comprise a period between 1 second and 60 seconds, and the second time period can comprise a period of at least 0.1 seconds In some embodiments, the first time period can comprise a period between 3 seconds and 20 seconds, and the second time period can comprise a period of at least 0.1 seconds. In some embodiments, the first time period can comprise a period of approximately 9 seconds, and the second time period can comprise a period of approximately 0.5 seconds. In any of these embodiments, the control module can further operate the fluid drive module at a third speed for a third time period where the third time period can comprise a period approximately the same duration as the second time period.

The second time period can comprise a period between 1% and 50% of the duration of the first time period. The second time period can comprise a period between 3% and 10% of the duration of the first time period. The second time period can comprise a period of approximately 5% of the duration of the first time period.

The second time period can comprise a period of approximately 0.5 seconds. The second time period can comprise a period less than 10 seconds.

The control module can further operate the fluid drive module at a third speed for a third time period. The third time period can approximate the duration of the second time period. The third time period can comprise a period of at least 0.1 seconds. The third time period can comprise a period of approximately 0.5 seconds. The third time period can comprise a period less than 10 seconds.

The control module can operate the fluid drive module in a continuous series of changing speeds, for example a series of repeated sets of similar speeds. The continuous series of changing speeds can comprise a first set of changing speeds performed at a first frequency and a second set of changing speeds performed at a similar or dissimilar second frequency.

The control module can be positioned outside the patient. The control module can comprise a power supply.

The fluid drive module can be constructed and arranged to provide a flow rate of at least 0.3 liters per minute. The fluid drive module can be constructed and arranged to provide a flow rate between 2 liters per minute and 6 liters per minute. The fluid drive module can be constructed and arranged to provide a flow rate of at least 6 liters per minute. The fluid drive module can be constructed and arranged to provide a flow rate of at least 7 liters per minute.

The fluid drive module can comprise a motor constructed and arranged to rotate the fluid drive element. The fluid drive module can further comprise a magnetic coupling, and the motor can rotate the fluid drive element via the magnetic coupling. The motor can comprise an electric motor.

The fluid drive element can comprise an impeller. The impeller can comprise a first arm, a second arm, and an opening therebetween, where the first arm and the second arm can be constructed and arranged to propel fluid. At least one of the multiple first speed flow vectors can be positioned in the opening, and the second speed can be constructed and arranged to modify said at least one of the multiple first speed flow vectors. Alternatively or additionally, the fluid drive element can comprise an element selected from the group consisting of: an Archimedes screw; a gear pump; a peristaltic pump; a balloon pump; and combinations of these.

The housing can comprise a tubular portion that circumferentially surrounds the fluid drive element.

The chamber can comprise a volume less than or equal to 100 ml. The chamber can comprise a volume less than or equal to 50 ml. The chamber can comprise a volume less than or equal to 10 ml. The chamber can comprise a volume less than or equal to 5.0 ml. The chamber can comprise a volume less than or equal to 2.5 ml. The chamber can comprise a volume less than or equal to 1.2 ml.

The system can further comprise a rotational drive assembly constructed and arranged to rotate the fluid drive element, where the chamber can comprise a gap positioned between the fluid drive element and the rotational drive assembly. At least one of the multiple first speed flow vectors can be positioned within the gap, and the second speed can be constructed and arranged to modify said at least one of the multiple first speed flow vectors.

The chamber can comprise an inflow port and an outflow port and, the multiple first speed flow vectors can comprise at least one retrograde flow vector oriented relatively toward the inflow port. The second speed can be constructed and arranged to modify the at least one retrograde flow vector to be oriented relatively away from the inflow port.

The system can further comprise a shaft with an end portion, where the shaft can pass through at least a portion of the fluid drive element. At least one of the multiple first speed flow vectors can be positioned proximate the shaft end portion, and the second speed can be constructed and arranged to modify said at least one of the multiple first speed flow vectors. The system can further comprise a gap between the fluid drive element and the shaft, where at least one of the multiple first speed flow vectors can be positioned within the gap, and the second speed can be constructed and arranged to modify said at least one of the multiple first speed flow vectors.

The system can further comprise at least one sensor where the system can be constructed and arranged to change from the first speed to the second speed based on at least one signal from the at least one sensor. The at least one sensor can comprise multiple sensors. The at least one sensor can be positioned at a first location, and the at least one sensor can be constructed and arranged to provide a signal correlating to the flow of blood proximate said first location. The sensor can comprise a sensor selected from the group consisting of: a flow sensor; an ultrasound sensor; a pressure sensor; a temperature sensor; an optical sensor; a magnetic sensor; an electromagnetic sensor; a current sensor; and combinations of these. The at least one sensor can comprise a sensor mounted to the housing and/or within the chamber. The system can further comprise an inflow cannula and/or an outflow cannula in fluid communication with the chamber, and the at least one sensor can comprise a sensor mounted to and/or within the inflow and/or outflow cannula.

The system can further comprise an inflow cannula in fluid communication with the chamber. The system can further comprise an outflow cannula in fluid communication with the chamber.

The system can further comprise a functional element comprising a component or assembly selected from the group consisting of: a power supply such as a battery or a capacitor; a sensor such as a fluid flow sensor, a pressure sensor, and/or an electromagnetic sensor; a cooling element; a heating element; a drug delivery device; and combinations of these.

According to another aspect of the present inventive concepts, a fluid flow system for a patient includes a control module and a fluid drive module including a fluid drive element; a housing surrounding the fluid drive element; and a chamber located between the housing a fluid drive element. The control module operates the fluid drive module at a first speed for a first time period, where the first speed generates a first speed flow pattern comprising multiple first speed flow vectors and further operates the fluid drive module at a second speed for a second time period, where the second speed is constructed and arranged to modify one or more of the multiple first speed flow vectors.

According to another aspect of the present inventive concepts, a blood flow system includes a fluid drive module including a fluid drive element, a housing surrounding the fluid drive element, and a chamber located between the housing and the fluid drive element; a control module which controls a rotational speed of the fluid drive element; a sensor assembly constructed and arranged to analyze the flow signal; and an algorithm constructed and arranged to analyze the flow signal. The control module changes the speed of the fluid drive element based on the algorithm analysis.

The sensor assembly can comprise multiple sensors.

The sensor assembly can comprise one or more sensors which produce a signal representing a current delivered to the fluid drive module. The rotational speed can be changed when the current delivered to the fluid drive module falls to 95% of a nominal level, for example to 90% of a nominal level. The rotational speed can be changed when the current delivered to the fluid drive module falls to a level indicative of a low flow condition.

The sensor assembly can comprise an encoder constructed and arranged to provide a signal indicative of rotation of at least a portion of the fluid drive module. The encoder can comprise a rotary encoder.

The sensor assembly can comprise at least one fluid flow sensor constructed and arranged to measure flow of fluid through a flow conduit. The at least one fluid flow sensor can comprise an ultrasonic sensor. The at least one fluid flow sensor can be positioned to measure flow through the fluid drive module chamber. The system can further comprise an inflow cannula and an outflow cannula, and the at least one fluid flow sensor can be positioned to measure flow through a location selected from the group consisting of: the inflow cannula; the outflow cannula; and combinations of these. The at least one fluid flow sensor can be positioned to measure flow through a location within the patient, for example, a heart chamber; a heart atrium; an artery; and combinations of these.

The algorithm can detect a suction condition. The algorithm can detect a low-flow condition.

The algorithm can change the rotational speed of the fluid drive element based on detection of a low-flow condition, for example where the low-flow condition comprises an average flow level below a threshold.

The algorithm can change the rotational speed of the fluid drive element from an operating speed to a second speed, where the second speed is less than the operating speed, for example 90% or less than the operating speed.

The algorithm can compare two or more flow assessments, and the rotational speed can be changed based on the comparison. The two or more flow assessments can comprise two or more assessments of average flow over a time period.

The algorithm can compare an assessment of average flow during a first time period to an assessment of average flow during a second time period, where the second time period is longer than the first time period and where the rotational speed of the fluid drive element is changed when the ratio of the average flow during the first time period to the average flow during the second time period falls below a threshold. The first time period can be at least 5 seconds, and the second time period can be at least 1 minute, such as when the first time period is at least 10 seconds, and the second time period is at least 3 minutes. The threshold can be approximately 0.85 or less. The algorithm can compare the assessment of the average flow during a first time period and the average flow during a second time period multiple times. The algorithm can perform the assessments three or more times, with a time period of at least 5 seconds between the initiation of each assessment. The algorithm can perform the assessment after a time period of at least 1 minute since the rotational speed of the fluid drive element was last changed.

The algorithm can compare an assessment of average flow during a first time period to an assessment of average flow during a second time period to produce a first ratio, and the algorithm can further compare an assessment of average flow during a third time period to the average flow during the second time period to produce a second ratio, where the second time period can be longer than the first and third time periods, and where the rotational speed of the fluid drive element can be changed when the first ratio and the second ratio fall below and first threshold and a second threshold. The first time period can be approximately the same duration as the third time period. For example, the first time period and the third time period can be at least 5 seconds, such as at least 10 seconds, and the second time period can be at least 1 minute, such as at least 3 minutes. A second example is where the first time period and the third time period can be at least 1 minute, such as at least 3 minutes, and the second time period can be at least 30 minutes, such as at least 90 minutes.

The algorithm can activate a restart function that reduces the rotational speed of the fluid drive element and subsequently increases the rotational speed of the fluid drive element. For example, the algorithm can activate the restart function when a low-flow condition is detected. The algorithm can reduce the rotational speed of the fluid drive element to approximately 0 rpm, for example for at least 2 minutes. The increase in rotational speed can be to a rotational velocity approximating the rotational velocity maintained just prior to the reduction of the rotational speed. The increase in rotational speed can be to a rotational velocity less than the rotational velocity just prior to the reduction of the rotational speed, for example 90% or less than the rotational velocity just prior to the reduction of the rotational speed. The increase in rotational speed can be to a rotational velocity less than the rotational velocity just prior to the reduction of the rotational speed if the restart function has been previously initiated at least once. The increase in rotational speed can be to a rotational velocity less than the rotational velocity just prior to the reduction of the rotational speed if the restart function has been previously initiated at least three times.

According to another aspect of the present inventive concepts, a method of providing blood flow to a patient includes: providing a blood flow system comprising a control module, a fluid drive module comprising a fluid drive element, a sensor assembly constructed and arranged to provide one or more blood flow signals to the control module, an alert module, and an algorithm constructed and arranged to analyze the one or more blood flow signals and activate the alert module based on the analysis; implanting at least the fluid drive module in the patient; and performing a patient event when the alert module is activated.

The patient event can comprise the patient drinking fluids, for example 1 to 5 liters of fluids.

The patient event can comprise a clinician performing a diagnostic procedure. The diagnostic procedure can comprise a procedure diagnosing filling and/or pumping volume of one or more chambers of the patient's heart. The diagnostic procedure can be selected from the group consisting of: trans-thoracic echocardiogram; trans-esophageal echocardiogram; CAT Scan; chest x-ray; ultrasound such as Doppler ultrasound; anti-coagulation level test; average clotting time test; pulmonary capillary wedge pressure (PCWP) test; pulmonary artery pressure (PAP) test; hemolysis test such as a plasma free hemoglobin test; cardiac output test; stress test such as a patient positional stress test; and combinations of these.

The blood flow system can further comprise an inflow cannula comprising a tip and an outflow cannula comprising a tip, and the patient event can comprise confirmation of the position of the inflow cannula tip and/or the outflow cannula tip. The confirmation can be performed using an imaging procedure selected from the group consisting of: Fluoroscopy; CtScan; Ultrasound such as transesophageal echocardiogram; and combinations of these.

The patient event can comprise delivering a drug or other agent to the patient, for example a blood thinning agent.

The patient event can comprise the patient changing a rest position, for example a sleep position.

The algorithm can activate the alert module when a low-flow condition is detected. The low-flow condition can be caused by any one of: insufficient fill from the patient's left atrium; a kink in an inflow cannula; a kink in an outflow cannula; or an obstruction in a blood flow path such as an obstruction present in a component of the blood flow system. The algorithm can activate the alert module when a high-flow condition is detected. The algorithm can activate the alert module when a fluid drive element high-speed condition is detected. The algorithm can activate the alert module when a fluid drive element low-speed condition is detected.

BRIEF DESCRIPTION OF THE DRAWINGS

FIG. 3A is a detailed view of the rotor of FIG. 3, consistent with the present inventive concepts.

DETAILED DESCRIPTION OF THE DRAWINGS

Figure 1:
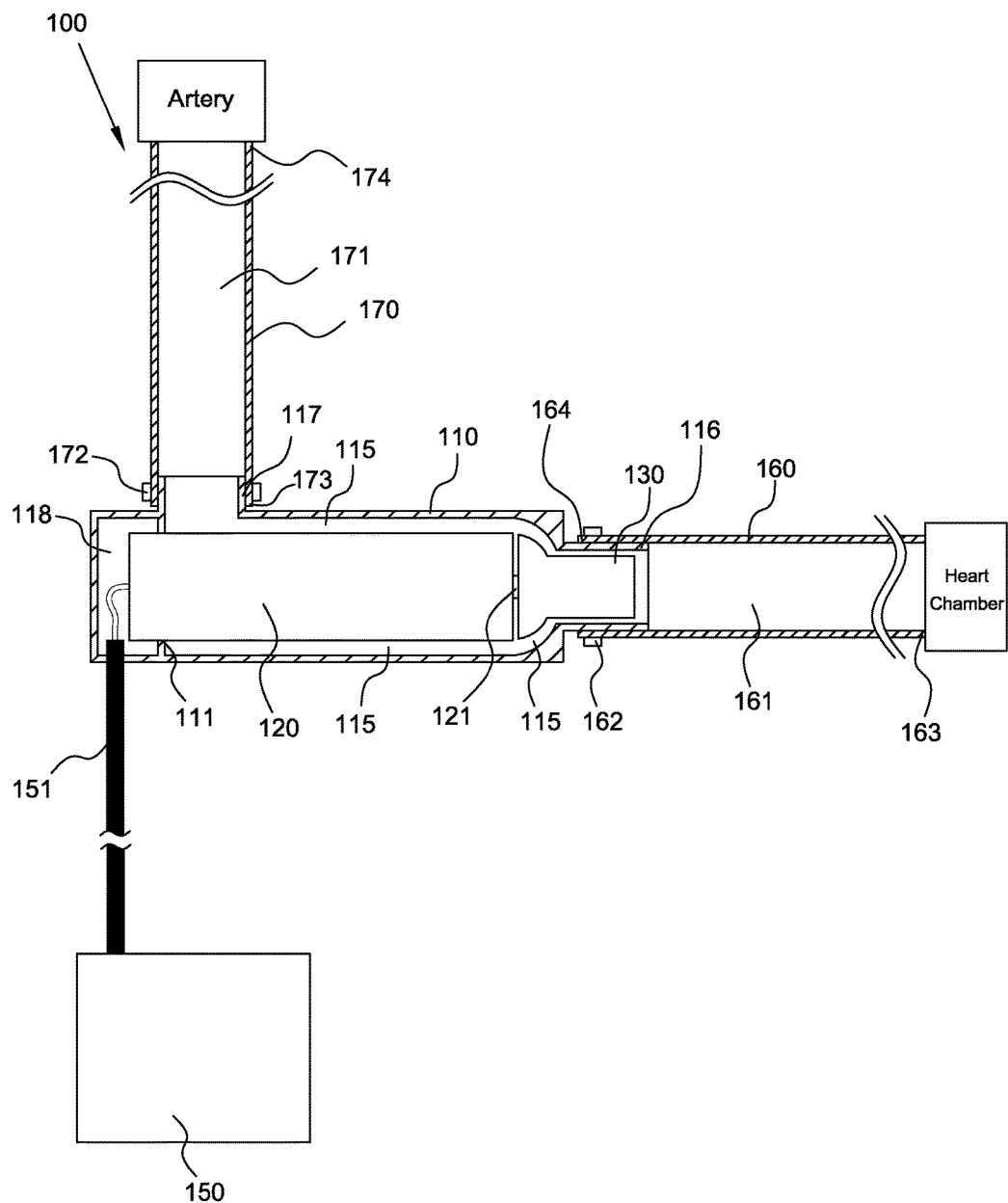
FIG. 1 is a schematic illustration of a fluid flow system for a patient, consistent with the present inventive concepts.

Reference will now be made in detail to the present embodiments of the invention, examples of which are illustrated in the accompanying drawings. The same reference numbers are used throughout the drawings to refer to the same or like parts.

The terminology used herein is for the purpose of describing particular embodiments and is not intended to be limiting of the inventive concepts. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element or intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between"

versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Provided herein are blood flow and other fluid flow systems, methods and devices for a patient, such as a mammalian patient. A blood flow system can be implanted or partially implanted in a patient to circulate blood through the cardiovascular system. The systems, methods and devices of the present inventive concepts are constructed and arranged to continuously or intermittently eliminate points of flow stasis or other low-flow areas that may serve as a nidus for thrombus formation. The systems of the present invention include rotational drive assemblies, such as motors, and fluid drive elements such as rotors, typically configured to pump bodily fluids such as blood. The fluid drive elements are rotated at target rotational velocities, also referred to herein as "speeds", typically between a minimum and maximum level. A normal or "operational" speed can be adjusted on a routine basis, such as to modify flow parameters to prevent an undesired flow condition, or on an as-needed basis such as when an undesired flow condition is encountered. As used herein, the terms "rotational velocity" and "speed" may be used interchangeably to describe an intended velocity (e.g. a programmed velocity), a measured velocity, and/or an actual velocity.

Referring now to FIG. 1, a schematic view of a fluid flow system is illustrated, consistent with the present inventive concepts. System 100, typically a blood flow system, includes a housing 110 surrounding a rotational drive assembly including motor 120 and fluid drive element 130. In some embodiments, system 100 comprises a rotational drive assembly similar to that described in U.S. patent Ser. No. 09/202,538, entitled "Blood Pump", filed Dec. 16, 1998 or an assembly as is described in U.S. patent Ser. No. 09/155,818, entitled "Intravascular Blood Pump", filed Oct. 5, 1998, the contents of which are each incorporated herein by reference in their entirety. Fluid drive element 130, typically an impeller, is engaged to motor 120, typically an electromagnetic motor, by shaft 121 such that fluid drive element 130 can be rotated by motor 120. Fluid drive element 130 can comprise a rotor, such as rotor 131 described in reference to FIG. 3 herebelow, or it can comprise another fluid drive element selected from the group consisting of: an Archimedes screw; a gear pump; a peristaltic pump; a balloon pump; and combinations of these. Fluid drive element 130 can be rotated by direct drive of shaft 121, or it can be rotated about shaft 121 by a magnetic coupling, such as a rotating magnetic field that engages one or more magnetic portions of drive element 130. In an alternative embodiment, fluid drive element 130 is magnetically levitated, avoiding the need for shaft 121. A space, chamber 115, includes the open space between housing 110 and the components surrounded by a tubular portion of housing 110, such as motor 120, fluid drive element 130 and shaft 121. A sealing surface, seal 111, circumferentially surrounds a portion of motor 120 such as to prevent fluid from passing into space 118. In some embodiments, chamber 115 comprises a volume less than 100 mL, for example less than 50 mL. In some embodiments, chamber 115 comprises a volume less than 10 mL, for example less than 5 mL, such as less than 2.5 mL or less than 1.2 mL.

Housing 110 comprises two ports, inlet port 116 and outlet port 117. When fluid drive element 130 is rotated, fluid propulsion forces are generated such that fluid flows from inlet port 116 to outlet port 117 through chamber 115. A hollow tube, inlet cannula 160 includes proximal end 163, distal end 164 and lumen 161 therebetween. Inlet cannula 160 is attached and/or is attachable to inlet port 116 at its distal end 164, such as via a compression fitting, fitting 162. In some embodiments, proximal end 163 of inlet cannula 160 is configured to be fluidly attached to a source of blood, such as a source of oxygenated blood, such as the left atrium or left ventricle of a patient. In some embodiments, inlet cannula 160 is configured as described in applicant's co-pending U.S. patent application Ser. No. 12/392,623, entitled "Devices, Methods and Systems for Establishing Supplemental Blood Flow in the Circulatory System", filed Feb. 25, 2009, the contents of which is incorporated herein by reference in its entirety.

A second hollow tube, outlet cannula 170 includes proximal end 173, distal end 174 and lumen 171 therebetween. Outlet cannula 170 is attached and/or is attachable to outlet port 117, such as via a compression fitting, fitting 172. In embodiments wherein inlet cannula 160 is attached to a source of arterial blood, distal end 174 of outlet cannula 170 can be configured to be fluidly attached to a blood vessel, such as an artery, such as via an anastomosis. In some embodiments, outlet cannula 170 can comprise an anastomotic connector on its distal end 174, such as is described in Applicant's U.S. Pat. No. 8,333,727, entitled "Two Piece Endovascular Anastomotic Connector", the contents of which is incorporated herein by reference in its entirety.

System 100 further includes a control module 150, which is operably attached to cable 151. Housing 110, inlet cannula 160 and outlet cannula 170 are typically implanted in the patient while control module 150 can remain outside the patient such that cable 151 travels through the skin of the patient to implanted housing 110. Cable 151 passes through housing 110 and is operably attached to motor 120, such as to control the rotational velocity of fluid drive element 130. Fluid drive element 130 can be rotated between one or more ranges of acceptable rotational velocities.

Figure 3:
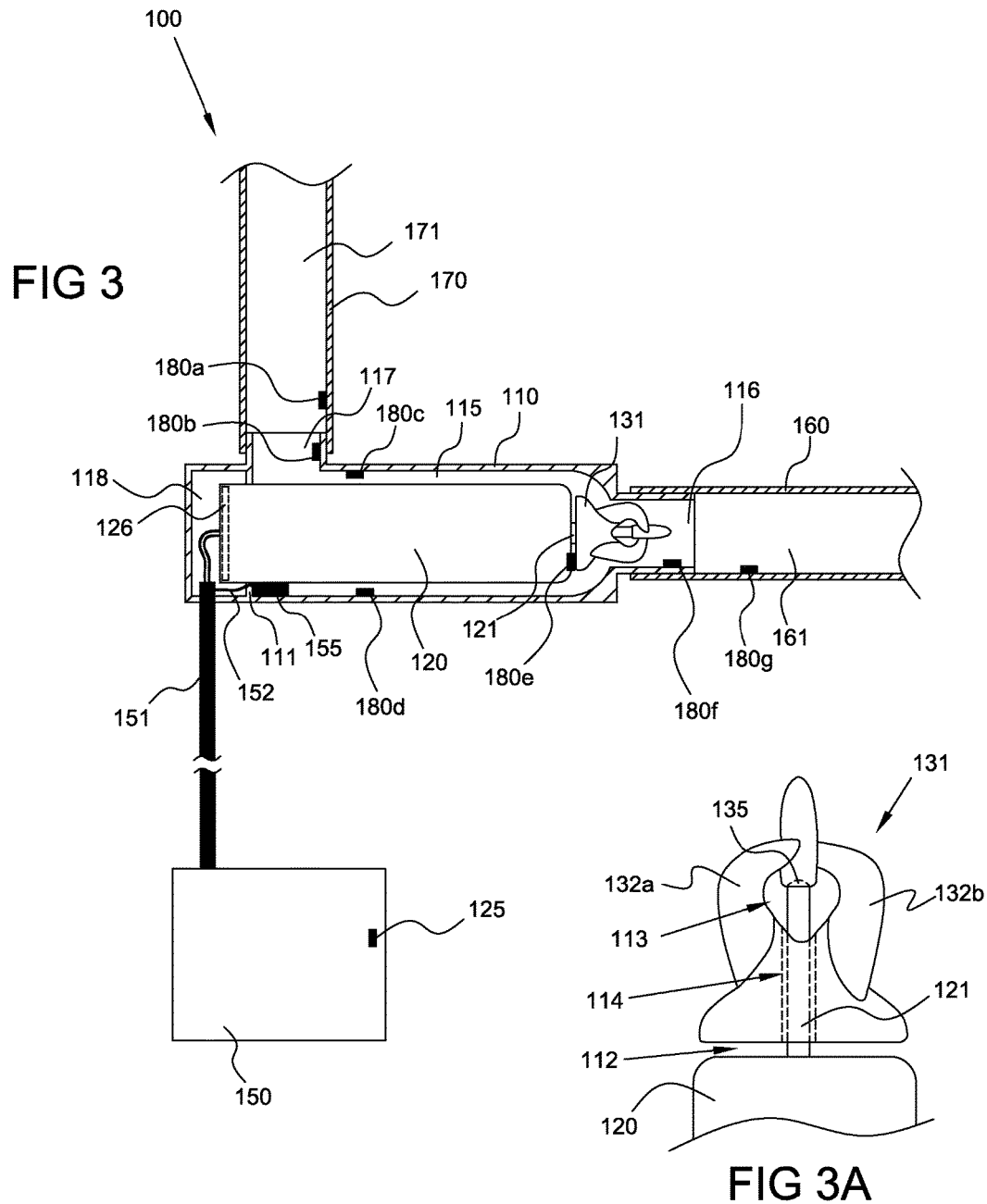
FIG. 3 is a schematic illustration of a fluid flow system for a patient including multiple flow sensors, consistent with the present inventive concepts.

Cable 151 can be additionally attached to one or more other components of system 100 contained on, in and/or within housing 110, additional components not shown but described in detail in reference to FIG. 3 herebelow.

Control module 150 includes various electronic components, firmware, hardware and software to allow variable rotational speed control of motor 120. Control module 150 can be configured to allow an operator of the system, such as a clinician of the patient receiving system 100, to adjust the rotational velocity of fluid drive element 130 and thus adjust the flow rates of fluid pumped through system 100. Alternatively or additionally, control module 150 can be configured to automatically adjust the rotational velocity or speed of fluid drive element 130, such as to change the magnitude and/or direction of the various patterns of flow, hereinafter "flow vectors". These flow vectors to be modified can be located in, on and/or proximate to one or more components of system 100, such as chamber 115, inlet cannula 160 and/or outlet cannula 170. Alternatively or additionally, these flow vectors can be located outside of one or more of the components of system 100, but within the patient, such as one or more locations within an organ such as the heart and/or within a blood vessel of the patient. The speed changes made by control module 150 can be initiated by an operator or by one or more internal algorithms, such as the algorithms described in reference to FIGS. 2, 4, 5, and 6 herebelow. One or more speed modifications can be performed during the use of system 100. In some embodiments, a particular configuration of speed modifications, or a particular configuration of a set of speed modifications is performed multiple times. In these embodiments, the single and/or multiple speed modifications can be temporally driven, such as multiple speed changes that are continuously repeated on a pre-determined, timed or otherwise synchronized basis. Alternatively or additionally, speed changes can be initiated by a planned or unplanned event, such as a speed modification initiated based on a signal received from one or more sensors, such as are described in reference to FIG. 3 herebelow. In some embodiments, system 100 performs a first set of speed modifications that are repeated at a first frequency (e.g. approximately once every 10 seconds), and a second set of speed modifications that are repeated at a second frequency (e.g. approximately once every hour). The first frequency and the second frequency can be similar or dissimilar frequencies.

In some embodiments, fluid drive element 130 and motor 120 are constructed and arranged to achieve a flow rate of blood of at least 0.3 L/min. In some embodiments, the system is configured to provide a flow rate of blood between 2.0 and 6.0 L/min. In other embodiments, the flow rate provided is at least 6.0 L/min, such as a flow rate at least 7.0 L/min.

Figure 2:
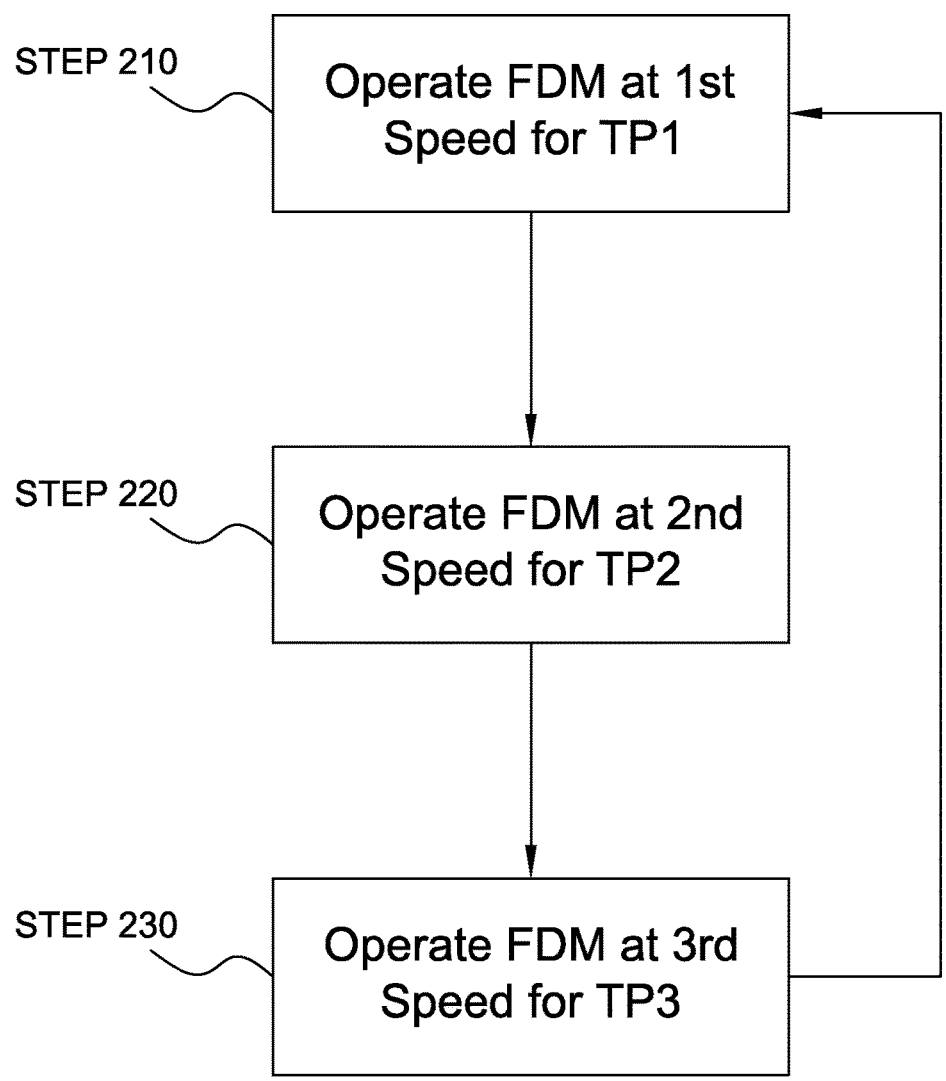
FIG. 2 is a flow chart of a rotational velocity modifying algorithm for a fluid flow system for a patient, consistent with the present inventive concepts.

Referring now to FIG. 2, a flow chart of a rotational velocity modifying algorithm for a fluid flow system is illustrated, consistent with the present inventive concepts. In STEP 210, a fluid drive module of a fluid flow system is operated at a first rotational velocity for a first time period, TP1. The fluid flow system can be fluid flow system 100 described in detail in reference to FIG. 1 and/or FIG. 3 herein, including a fluid drive element, such as fluid drive element 130 of FIG. 1 and/or rotor 131 of FIG. 3. Rotation of the fluid drive module at the first velocity causes fluid to flow through the system, and results in a three dimensional array of first speed flow vectors present throughout various flow paths within the system (e.g. within a housing, inlet cannula and outlet cannula) and/or within the patient (e.g. within a heart chamber or blood vessel of the patient in which blood flow is enhanced or otherwise modified by the system). Each flow vector represents a magnitude and direction of flow at a point in three dimensional space.

In STEP 220, the rotational velocity is modified to a second speed for a second time period, TP2. As a result of the speed change, one or more of the first speed flow vectors are modified, in other words, the magnitude and/or direction of flow is changed at the one or more flow vector locations. During operation at the second speed, a three dimensional array of second speed flow vectors is created throughout the various flow paths within the system and/or within one or more anatomical locations influenced by the system. The second speed can be greater than the first speed or less than the first speed. In some embodiments, the fluid flow system can be operated between a minimum speed and a maximum speed, and the first speed can comprise a speed between the minimum and maximum speeds while the second speed approximates the minimum or maximum speed.

In an optional STEP 230, the rotational velocity is modified to a third speed for a third time period, TP3. As a result of the speed change, one or more of the first speed flow vectors and/or second speed flow vectors is modified. During operation at the third speed, a three dimensional array of third speed flow vectors is created throughout the various flow paths within the system and/or within one or more anatomical locations influenced by the system. In some embodiments, the fluid flow system can be operated between a minimum speed and a maximum speed, and the first speed can comprise a speed between the minimum and maximum speeds while the second speed approximates the minimum or maximum speed, and the third speed approximates the opposite extreme (e.g. maximum or minimum) than that approximated by the second speed.

In some embodiments, system 100 performs steps 210 and 210, and optionally step 230, repeatedly at a first frequency (e.g. approximately once every 10 seconds). In these embodiments, a second set of speed modifications, such as a second set of steps 210 and 220, and optionally step 230, can be performed repeatedly at a second frequency, (e.g. approximately once every hour). The first frequency and the second frequency can be similar or dissimilar frequencies. The second set of speed modifications can be continuously repeated on a pre-determined, timed or otherwise synchronized basis as described above. Alternatively, a speed modification can be initiated by a planned or unplanned event, such as speed modification initiated based on a signal received from one or more sensors, such as are described in reference to FIG. 3 herebelow. In some embodiments, additional (e.g. third and fourth) repeated performance of different steps 210 and 220, and optionally step 230, can be performed by system 100, such as to create multiple overlays of changing speed patterns repeated at different time intervals.

Modification of a flow vector by changing speed can include a velocity change to that flow vector. Velocity changes can include an increase from a low-flow condition such as an increase in flow at a location with near-zero flow (e.g. a stasis point). In blood flow systems, locations with low flow are likely to result in clotting after a relatively short time period. The resultant increase in flow (e.g. due to the change to the second speed of STEP 220 and/or the third speed of STEP 230) can be configured to prevent creation of undesired blood thrombus or other solidified material, such as a thrombus or other material that might occlude a portion of the system and/or deliver an embolus of solid material to the patient (e.g. one or more embolus that could result in a stroke or other ischemic event).

Alternatively or additionally, modification of a flow vector by changing speed can include a change in direction of flow at one or more locations. Changes in flow direction can be used to "wash" a surface (e.g. remove collected material from a surface) and/or disrupt low or stagnant flow locations (e.g. increase flow in one or more low-flow locations). Changes in flow direction can be configured to provide a function selected from the group consisting of: reducing or preventing cell adhesion; reducing or preventing protein adhesion; reducing or preventing cellular aggregation; reducing or eliminating a nidus for thrombus formation; reducing or preventing eddy currents; reducing or preventing a zone of stagnant flow; reducing or preventing a steady state flow; enhancing volume loading of an atrium of the heart; allowing volume loading of an atrium of the heart: and combinations of these.

In some embodiments, STEPS 210 through 220 and/or STEPS 210 through 230 are continuously repeated, such that the fluid drive element continuously cycles between the first speed and the second speed, or it cycles between the first speed, the second speed and the third speed.

In some embodiments, the fluid flow system allows the speed to be set (e.g. automatically or manually) to a level between a minimum speed and a maximum speed. In some embodiments, the minimum speed is 100 rpm, such as when the maximum speed is 100,000 rpm. In other embodiments, the minimum speed is 5,000 rpm, such as when the maximum speed is 50,000 rpm. In yet other embodiments, the minimum speed is 20,000 rpm while the maximum speed is 28,000 rpm. In these embodiments, the first speed, the operating speed, can be set to a rotational velocity between 21,000 rpm and 27,000 rpm, while the second speed can approximate the maximum, 28,000 rpm and the third speed, if used, can approximate the minimum, 20,000 rpm. Alternatively in these particular embodiments, the second speed can approximate the minimum, 20,000 rpm and the third speed, if used, can approximate the maximum, 28,000 rpm.

In some embodiments, the second speed is proportionally faster than the first speed, such as a second speed that is between 1% and 100% faster than the first speed (i.e. 1.01 to 2.0 times the first speed). In some embodiments, the second speed is between 5% and 75% faster than the first speed. In some embodiments, the second speed is between 10% and 50% faster than the first speed. In some embodiments, the second speed is up to 40% faster than the first speed.

In some embodiments, the second speed is proportionally slower than the first speed, such as a second speed that is between 1% and 99% of the first speed (i.e. 0.01 to 0.99 times the first speed). In some embodiments, the second speed is between 25% and 95% of the first speed. In some embodiments, the second speed is between 50% and 90% of the first speed. In some embodiments, the second speed is between 60% and 99% of the first speed.

Time periods TP1, TP2 and potentially TP3 can comprise time periods of various temporal durations. In some embodiments, TP1 has a duration between 1 second and 1 hour, while time periods TP2 and potentially TP3 have durations less than the duration of TP1. In some embodiments, TP1 has a duration between 1 second and 60 seconds, and TP2 has a duration of at least 0.1 seconds. In these embodiments, TP3 can have a duration similar to TP2, e.g. at least 0.1 seconds. In some embodiments, TP1 has a duration between 3 seconds and 20 seconds and TP2 has a duration of at least 0.1 seconds. In these embodiments, TP3 can have a duration similar to that of TP2, e.g. at least 0.1 seconds. In some embodiments, TP1 has a duration of approximately 9 seconds, and TP2 has a duration of approximately 0.5 seconds. In these embodiments, TP3 can have a duration similar to that of TP2, e.g. at least 0.5 seconds. In some embodiments, the duration of TP2 is proportionally less than TP1, such as when TP2 is between 1% and 50% of TP1, or when TP2 is between 3% and 10% of TP1, or when TP2 is approximately 5% of TP1. In some embodiments, TP2 comprises a duration of approximately 0.5 seconds. In other embodiments, TP2 comprises a duration less than 10 seconds. In some embodiments, TP3 approximates TP2 in duration. TP3 can be at least 0.1 seconds in duration and it can be less than 10 seconds in duration. In some embodiments, T3 approximates 0.5 seconds in duration.

Referring now to FIG. 3, a schematic view of a fluid flow system is illustrated, consistent with the present inventive concepts. System 100, typically a blood flow system, includes a housing 110 surrounding a rotational drive assembly, motor 120 and a fluid drive element, rotor 131. Rotor 131 is engaged with motor 120 by shaft 121 such that rotor 131 can be rotated by motor 120. A space, chamber 115, includes the open space between housing 110 and the components surrounded by housing 110, such as motor 120, rotor 131 and shaft 121. A sealing surface, seal 111, circumferentially surrounds a portion of motor 120 such as to prevent fluid from passing into space 118.

System 100 includes components similar to system 100 of FIG. 1, including: housing 110 including inlet port 116 and outlet port 117; inlet cannula 160 including lumen 161; and outlet cannula 170 including lumen 171. When rotor 131 is rotated, fluid propulsion forces are generated such that fluid flows from inlet port 116 to outlet port 117 through chamber 115.

System 100 further includes a control module 150, which is operably attached to cable 151. Housing 110, inlet cannula 160 and outlet cannula 170 are typically implanted in the patient while control module 150 can remain outside the patient such that cable 151 travels through the skin of the patient to implanted housing 110. Cable 151 passes through housing 110 and is operably attached to motor 120, such as to control the rotational velocity of rotor 131. Cable 151 is additionally attached to one or more sensors or other components or assemblies of system 100, such as sensors 180a, 180b, 180c, 180d, 180e, 180f, 180g and functional element 155.

Control module 150 includes various electronic components, firmware, hardware and software to allow variable rotational speed control of motor 120. Control module 150 can include a user interface, such as a user interface including data input and data output devices, such as screens, buttons, controls, lights, audible transducers, and the like. Control module 150 can be configured to allow an operator of the system, such as a clinician of the patient receiving system 100, to adjust the rotational velocity of rotor 131 and thus adjust the flow rates of fluid pumped through system 100. Alternatively or additionally, control module 150 can be configured to automatically adjust the rotational velocity of rotor 131, such as to change magnitude and/or direction of one or more flow vectors. These flow vectors to be modified can be present in one or more components of system 100, such as chamber 115, inlet cannula 160 and/or outlet cannula 170, as well as flow locations outside of system 100 but within the patient, such as one or more locations within a heart chamber or within a blood vessel of the patient.

Figure 4:
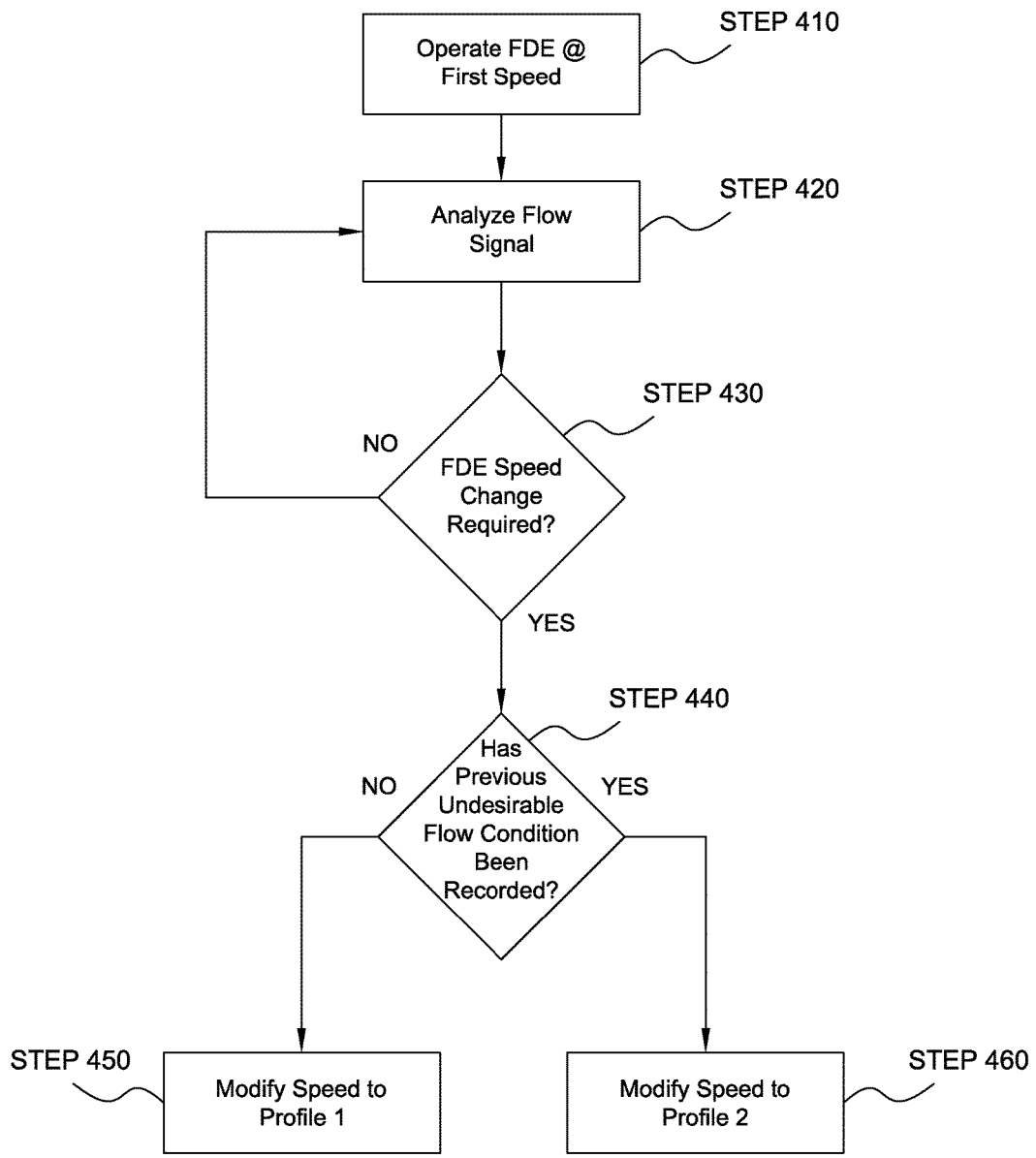
FIG. 4 is a flow chart of a rotational velocity modifying algorithm for a fluid flow system for a patient, consistent with the present inventive concepts.
Figure 5:
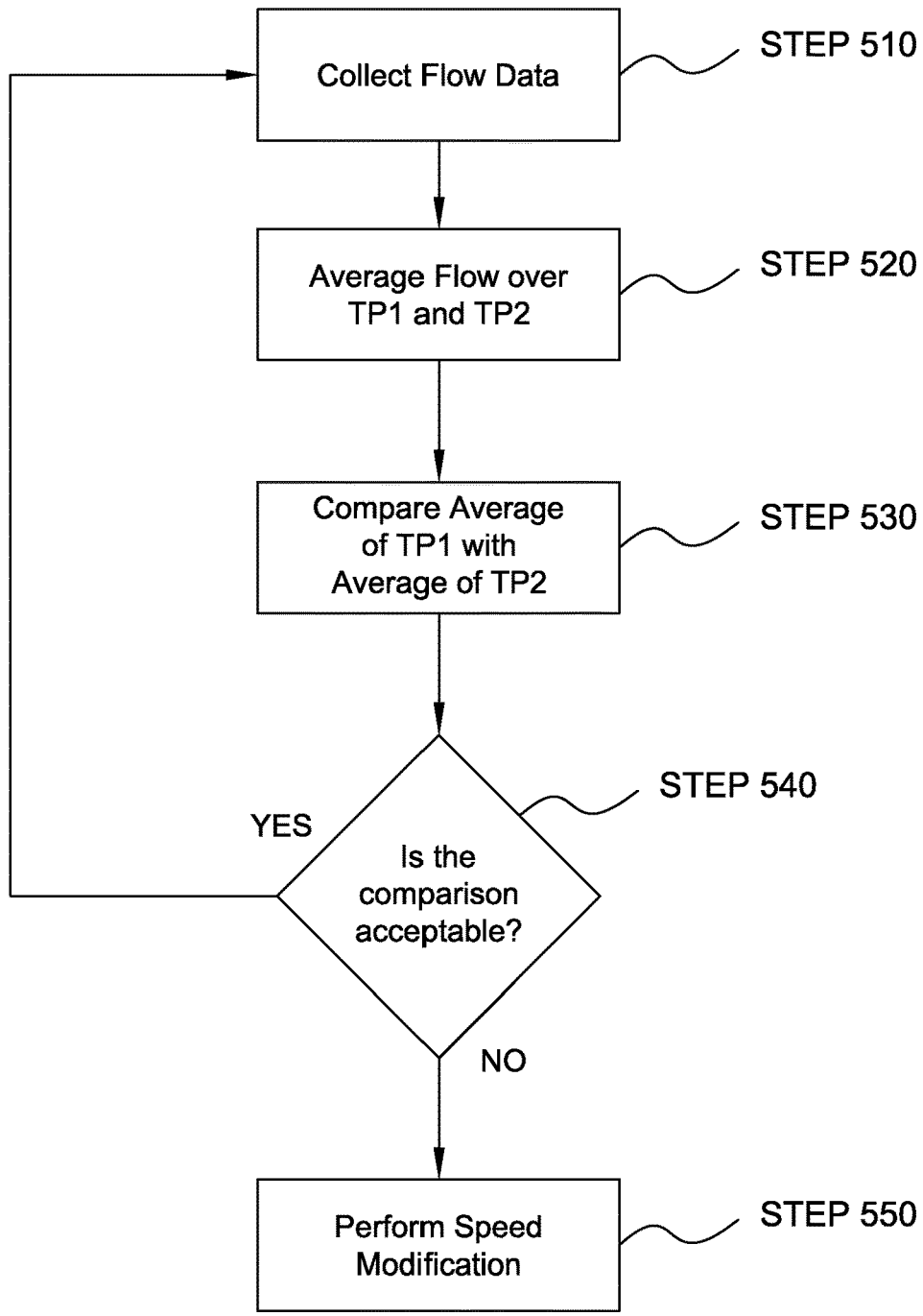
FIG. 5 is a flow chart of a rotational velocity modifying algorithm for a fluid flow system for a patient, consistent with the present inventive concepts.

Control module 150 can include one or more algorithms used to control and/or adjust the rotational velocity of rotor 131, such as the algorithms described in reference to FIGS. 2, 4, 5 and/or 6 described herein. Control module 150 can include an algorithm which utilizes information received from one or more of sensors 180a-g and/or functional element 155 to adjust one or more system operational parameters, such as the rotational velocity of rotor 131, as is described herebelow.

Sensors 180a-g are typically connected to cable 151 and control module 150 by one or more wires, wires not shown for illustrative clarity but typically one or more conductive conduits surrounded by electrically insulating material. Sensors 180a-g can be positioned in any location within or external to system 100, such as sensors positioned in the various locations shown in FIG. 3. Sensors 180a-g can be positioned to detect a flow condition in a location selected from the group consisting of: an area within lumen 161 of inlet cannula 160; an area proximate inlet port 116; an area proximate rotor 131; an area between rotor 131 and motor 120; an area between housing 110 and motor 120; an area proximate outlet port 117; an area proximate lumen 171 of outflow cannula 170; and combinations of these. Alternatively or additionally, one or more flow sensors can be placed outside of system 100 but within the patient, not shown but typically within a heart chamber or blood vessel of the patient. Sensors 180a-g can be ultrasonic flow sensors or other sensors that provide a signal representative of a flow condition such as a sensor selected from the group consisting of: a flow sensor; an ultrasound sensor; a pressure sensor; a temperature sensor; an optical sensor; a magnetic sensor; an electromagnetic sensor; a current sensor; and combinations of these.

In some embodiments, information received from one or more of sensors 180a-g and/or functional element 155 is used by control module 150 to cause a change in rotational velocity of rotor 131. Additionally or alternatively, information received from one or more sensors 180a-g and/or functional element 155 can be used to determine the effectiveness or other parameter of a speed change, such as to provide closed loop information in determining the magnitude of a rotational velocity change. In some embodiments, when a low-flow or stasis condition is detected, such as by a pressure or flow sensor, the speed is adjusted. Alternatively or additionally, when solid particulate matter is detected, such as by an optical sensor, the speed can be adjusted. Functional element 155 is connected to control module 150 via wires 152 and cable 151. Functional element 155 can comprise a sensor (e.g. one or more of the sensors described hereabove), a transducer, or other functional component or assembly. In some embodiments, functional element 155 comprises an element selected from the group consisting of: a power supply such as a battery or a capacitor; a sensor such as a fluid flow sensor, a pressure sensor, and/or an electromagnetic sensor; a cooling element; a heating element; a transducer such as an audio transducer or a tactile transducer; a drug delivery device such as a drug delivery device configured to deliver an anti-coagulant; and combinations of these.

In some embodiments, system 100 includes a means of monitoring current flow to motor 120, such as via current sensor 125 of control module 150. One or more algorithms of control module 150 can analyze current drawn by motor 120 to estimate actual rotational velocity of rotor 131. Alternatively or additionally, motor 120 can include a position sensing element, such as rotary encoder 126, typically positioned to monitor the position of one or more rotating components of motor 120.

System 100 of FIG. 3 can be configured to change speeds, such as repeatedly changing from a first speed to a second speed, or from a first speed to two or more other speeds, typically on a continuous or semi-continuous basis. In some embodiments, flow vectors that are oriented in a retrograde direction (i.e. oriented relatively toward inlet port 116) during operating speed conditions, are redirected by the change in speed, such as to become relatively oriented toward outlet port 117. Speed changes can be performed to cause a flow vector oriented in an antegrade direction to change to a retrograde direction, or to cause other flow vector directional changes. In some embodiments, speed changes are implemented to change flow vectors in certain areas, such as locations 112, 113 and 114 as shown in FIG. 3A.

Referring additionally to FIG. 3A, a magnified view of rotor 131 of FIG. 3 is illustrated. Rotor 131 is constructed and arranged to be rotated within a range of speeds while minimizing stasis or other low-flow areas proximate rotor 131. Rotor 131 includes two fluid propulsion blades, arms 132a and 132b. Motor 120 includes shaft 121 which is slidingly received by a lumen of rotor 131. Rotor 131 engages the distal end of shaft 121 at pivot point 135. Gap 112 comprises the space between the bottom surface of rotor 131 and motor 120. Gap 114 comprises the space between rotor 131 and shaft 121. Washout area 113 comprises the opening between arms 132a and 132b as shown. In some embodiments, washout area 113 comprises a heart-shaped cross section. Washout area 113 can be constructed and arranged to cause retrograde flow to occur in gap 114, such as a flow which enters gap 112, passing through gap 114, and exiting washout area 113. Fluid exiting washout area 113 can improve or otherwise modify the flow conditions at one or more locations proximate rotor 131, such as a modification which occurs as a result of a rotational speed change or otherwise.

Referring now to FIG. 4, a flow chart of a rotational velocity modification algorithm is illustrated, consistent with the present inventive concepts. The algorithm of FIG. 4 can comprise one or more algorithms maintained in a control module of a fluid flow system, such as control module 150 of fluid flow system 100 of FIG. 1 and/or FIG. 3 described hereabove. The system includes a fluid drive element, such as fluid drive element 130 of FIG. 1 and/or rotor 131 of FIG. 3. Rotation of the fluid drive element at a first speed causes fluid to flow through the system, and results in a three dimensional array of first speed flow vectors present throughout various flow paths within the system (e.g. within a housing, inlet cannula or outlet cannula) or within the patient (e.g. within a heart chamber or blood vessel of the patient in which flow is effected by the system). Each flow vector represents a magnitude and direction of flow at a point in three dimensional space.

In STEP 410, the fluid drive element (FDE) of the fluid flow system is operated at a first speed, also referred to as a normal or operating speed. The systems of the present invention can include a range of potential operating speeds, ranging between a minimum operating speed and a maximum operating speed. The clinician and/or the control module can be allowed to operate the system within these predetermined speed levels.

In STEP 420, one or more flow parameters are analyzed, such as by one or more sensors such as those described in reference to FIG. 3 hereabove. In some embodiments, a current sensor is used to provide a signal correlating to actual speed of the fluid drive element or otherwise diagnose an undesired flow condition. Undesired flow conditions can be represented by undesirably high or low speeds of the fluid drive element. In some embodiments, a current drop below 95% of normal, for example below 90% of normal such as 85% or lower of normal, is indicative of an issue to be resolved. Alternatively or additionally, one or more flow sensors, such as ultrasonic flow sensors or other sensors described hereabove, can be used to measure achieved flow in one or more locations within and/or external to the fluid flow system. Undesired flow conditions can include undesirably high-flow or low-flow conditions.

In STEP 430, results of the analysis of STEP 420 are used to determine if the speed of the fluid drive element should be modified. In a typical embodiment, indications of low flow, inadequate flow, suction condition, or otherwise undesired flow conditions can result in a speed change. Low-flow conditions can be caused by numerous factors including but not limited to: kinking of one or more flow conduits of the system (e.g. the inflow cannula or the outflow cannula), a suction condition or otherwise improper filling of the patient source of blood (e.g. improper filling of the chamber of the heart such as the left atrium), occlusion in the delivery point to the patient (e.g. occlusion in an artery into which the outflow cannula is connected); and combinations of these.

If a speed change is not required, the analysis of STEP 420 is repeated. The repetition of STEP 420 can be continuous, or at a scheduled time interval, such as every 30 seconds.

If a rotational velocity change is required, STEP 440 is performed in which any previously recorded undesired flow conditions are analyzed. Based on the number of previous occurrences of undesired flow conditions, the profile of a speed change can be determined. The profile of the fluid drive element speed change can comprise a series of different speed levels that result in a final, steady state rotational velocity.

In the embodiment of FIG. 4, if a previous undesired flow condition has not been detected, the speed is modified to a first speed profile in STEP 450. If a previous undesired flow condition has been detected, the speed is modified to a second speed profile in STEP 460, wherein the second speed profile is different than the first speed profile. In some embodiments, the velocity profile of STEP 450 is implemented if the number of undesired flow conditions detected is below a threshold, such as below 3 times, and STEP 460 is implemented if the undesired flow condition is at or above a threshold, such as at or above 3 times.

In some embodiments, a "start" or "restart" function can be employed wherein the first speed profile comprises an initial rotational velocity of zero, which is subsequently increased, e.g. after a wait period such as a wait period of at least two seconds, to the first speed of STEP 410, e.g. a normal operating speed set by a clinician. In those embodiments, a second speed profile can comprise an initial velocity of zero, which is subsequently increased to a second speed, the second speed being lower than the first speed of STEP 410, typically set to a minimum rotational velocity acceptable to the system and/or to a velocity that is 90% of the previous or operating speed of the system. In a particular set of embodiments, after two detections of undesired flow conditions, the fluid drive element is stopped and then increased to the original operating or first velocity. After the third undesired flow detection however, the system enters a safe mode in which the fluid drive element is stopped and subsequently restarted at a lower, typically a minimum rotational velocity. Activation of the restart function can cause one or more undesired flow conditions to be alleviated.

Referring now to FIG. 5, a flow chart of a speed modification algorithm is illustrated, consistent with the present inventive concepts. The algorithm of FIG. 5 can comprise one or more algorithms maintained in a control module of a fluid flow system, such as control module 150 of fluid flow system 100 of FIG. 1 and/or FIG. 3 described hereabove. The system includes a fluid drive element, such as fluid drive element 130 of FIG. 1 and/or rotor 131 of FIG. 3. Rotation of the fluid drive element at a first speed causes fluid to flow through the system, and results in a three dimensional array of first speed flow vectors present throughout various flow paths within the system (e.g. within a housing, inlet cannula or outlet cannula) or within the patient (e.g. within a heart chamber or blood vessel of the patient in which flow is effected by the system). Each flow vector represents a magnitude and direction of flow at a point in three dimensional space.

In STEP 510, the fluid drive element of the fluid flow system is operated at a first speed, also referred to as a normal or operating speed, while data representing quantitative or qualitative flow data is collected. In STEP 520, the collected data is averaged over a first time period, TP1, and a second time period, TP2. TP1 is typically of shorter duration than TP2. In STEP 530, the averaged data from TP1 and TP2 time periods is compared to produce a result, such as a ratio. In STEP 540, the result of the comparison is compared to a threshold, such as to confirm if it is above or below a threshold, or between a range defined by an upper and lower threshold. If the comparison results in an acceptable outcome, STEP 510 is repeated. If the comparison results in an unacceptable outcome, STEP 550 is performed in which a speed modification is performed, such as an increase or decrease in speed of the fluid drive element, typically a decrease in speed such as a decrease to a minimum system speed. Alternatively, multiple changes in speeds can be performed, such as the speed profile change described in reference to FIG. 4 hereabove. Alternatively or additionally, the speed modification performed can be selected from a group of potential speed modifications (or speed profile modifications) based on previous comparisons of results in previously performed STEPs 530 and 540, such as is described in reference to STEPs 440, 450 and 460 described in reference to FIG. 4 hereabove.

TP2 comprises a duration typically longer than TP1, such as a duration 5 to 20 times longer than TP1. Durations of TP2 and TP1 can be selected to identify and/or differentiate rapid and gradual flow changes that are undesired. In some embodiments, such as to detect a rapid flow change, TP1 comprises a duration of at least 5 seconds while TP2 comprises a duration of at least 60 seconds, or TP1 comprises a duration of at least 10 seconds while TP2 comprises a duration of at least 3 minutes. In other embodiments, such as to detect a more gradual flow change, TP1 comprises a duration of at least 1 minute and TP2 comprises a duration of at least 30 minutes, or TP1 comprises a duration of at least 3 minutes and TP2 comprises a duration of at least 90 minutes.

A flow change can be indicated in STEPs 530 and 540 when a comparison of averaged data collected during TP1 is compared to averaged data collected during TP2 and the difference in the two averages is significant (i.e. the ratio of the TP1 average and the TP2 average is below a threshold). In some embodiments, if the ratio of averaged values is below 95%, such as a ratio of 85% or lower, a flow change is made.

STEPs 510 through 540 can be repeated on a continuous or intermittent basis such as every 5 to 15 seconds, for example STEPs 510 through 540 can be performed at least three times with a time period of at least 2 minutes between the initiations of STEP 510. STEP 510 can be initiated at the initiation of fluid pumping, or after a delayed time period such as at least one minute after initiation of fluid pumping and/or at least one minute after each speed change. In other embodiments, STEP 510 can be initiated after a delayed time period such as at least 30 minutes after initiation of fluid pumping and/or at least 30 minutes after each speed change.

In alternative embodiment, during STEP 510, data is collected during a third time period, TP3, typically of similar duration to TP1, used in conjunction with TP1 to determine when a speed modification should be performed. In STEP 520, the data collected during TP3 is averaged. In STEP 530, the averaged data collected during TP3 is compared to similar averaged data collected during TP2. Alternatively or additionally, a comparison between TP3 data and TP1 data can be performed. In STEP 540, the decision to change speed can be based on the comparisons of one or both TP3 to TP2 and TP1 to TP2, e.g. when one or both relative ratios fall outside of an acceptable threshold (e.g. below one or two thresholds), the speed modification of STEP 550 is performed. In this particular embodiment, TP1 and TP3 time periods can approximate the time periods for TP1 described immediately hereabove, and the time period for TP2 can approximate the time periods for TP2 described immediately hereabove.

Figure 6:
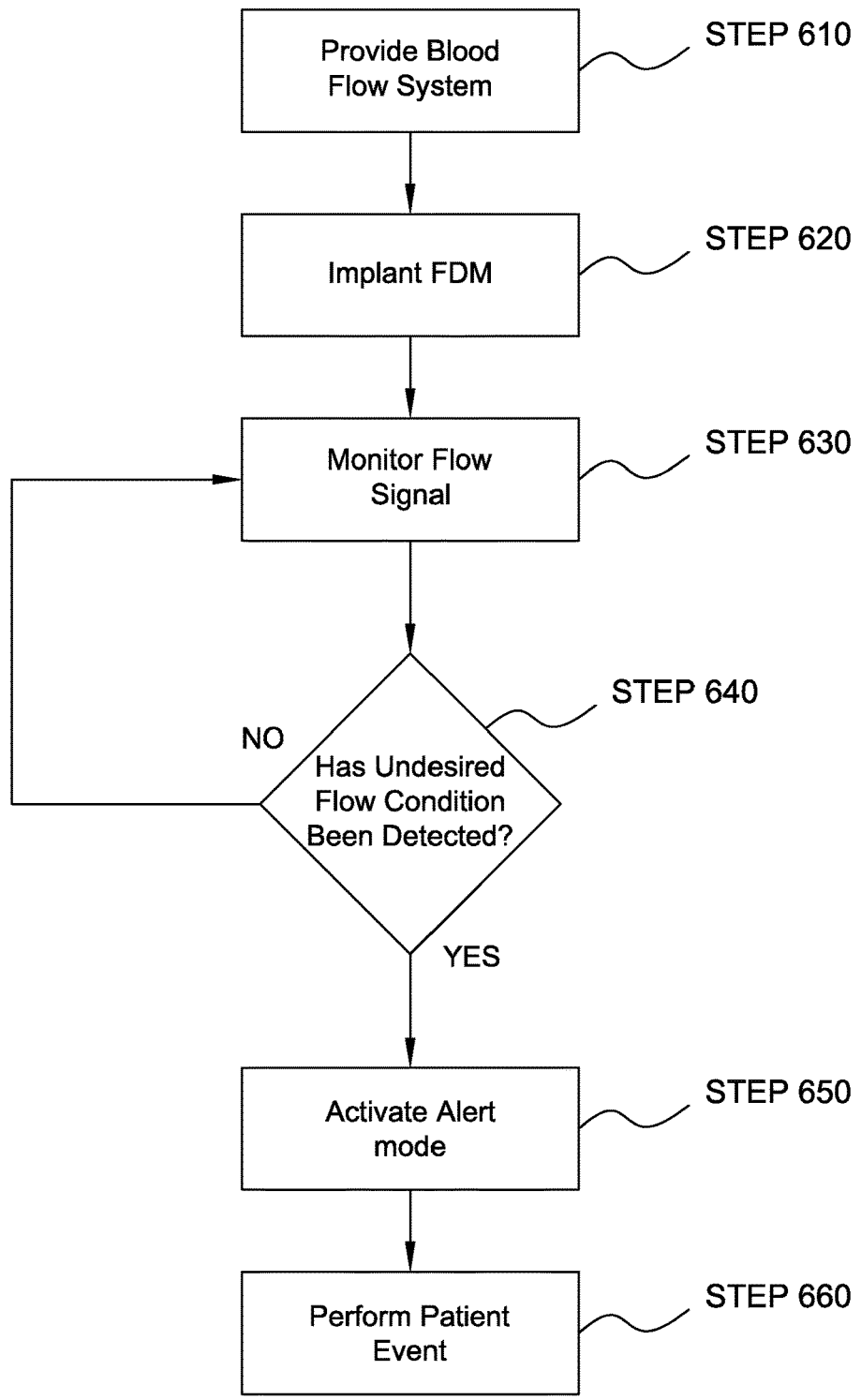
FIG. 6 is a flow chart of a method of treating a patient with a blood flow system, consistent with the present inventive concepts.

Referring now to FIG. 6, a flow chart of a method of treating a patient with a blood flow system is illustrated, consistent with the present inventive concepts. In STEP 610, a blood flow system is provided, such as fluid flow system 100 of FIG. 1 and/or FIG. 3 described hereabove. The system includes a fluid drive element, such as fluid drive element 130 of FIG. 1 and/or rotor 131 of FIG. 3. Rotation of the fluid drive element at a first speed causes fluid to flow through the system, and results in a three dimensional array of first speed flow vectors present throughout various flow paths within the system (e.g. within a housing, inlet cannula or outlet cannula) or within the patient (e.g. within a heart chamber or blood vessel of the patient in which flow is effected by the system). Each flow vector represents a magnitude and direction of flow at a point in three dimensional space.

In STEP 620, a fluid delivery module (FDM) is implanted in the patient, such as has been described in U.S. Pat. No. 6,116,862, entitled "Blood Pump", filed Aug. 31, 2010, the contents of which is incorporated herein by reference in its entirety. An inlet cannula is fluidly attached to a source of oxygenated blood, such as the patient's left atrium. An outlet cannula is fluidly attached to an artery of the patient, such as the subclavian artery.

In STEP 630, one or more flow parameters are monitored, such as has been described in detail hereabove. Numerous flow parameters can be monitored, such as flow parameters monitored by recording of data from one or more sensors of the blood flow system. In some embodiments, current delivered to a motor is monitored, where the motor drives a rotor or other fluid delivery element, and the modified current is indicative or rotational velocity of the rotor and/or loading placed on the rotor. In some embodiments, flow sensors such as ultrasonic flow sensors and/or pressure transducers are monitored, such as to detect a low-flow condition.

In STEP 640, the data collected in STEP 630 is analyzed, such as to be compared to a threshold or mathematically processed and compared to one or more thresholds. Mathematical processing includes but is not limited to: averaging; integrating; determining a peak; determining a mean; combining; filtering; and combinations of these. The results of the analysis indicate whether an undesired flow condition has been detected, such as the detection of a low-flow condition.

If an undesired flow condition is not detected, STEP 630 is repeated.

If an undesired flow condition is detected, STEP 650 is performed in which the blood flow system activates an alert mode. Activation of the alert mode can include activating one or more audible or visible transducers of an external device, such as control unit 150 of FIG. 1 and/or FIG. 3, or an internal alert transducer such as functional element 155 of FIG. 3. In one embodiment, the alert mode can be triggered when a low-flow condition is detected where the low-flow condition can be caused by numerous factors including but not limited to: kinking of one or more flow conduits of the system (e.g. the inflow cannula or the outflow cannula), a suction condition or otherwise improper filling of the patient source of blood (e.g. improper filling of the chamber of the heart such as the left atrium), occlusion in the delivery point to the patient (e.g. occlusion in an artery into which the outflow cannula is connected); and combinations of these.

Notified by the alert mode, in STEP 660, a patient event is performed, such as to remedy the undesired flow condition or ensure patient safety. In some embodiments, a patient event can comprise the patient drinking fluids, such as drinking between 1 and 5 liters of fluid. Additionally or alternatively, a patient event can comprise a diagnostic procedure being performed, either by the patient, caregiver, clinician, or the like. Diagnostic procedures can include monitoring the filling volume and/or pumping volume of one or more chambers of the heart. In some embodiments, diagnostic procedures can be selected from the group consisting of: trans-thoracic echocardiogram; trans-esophageal echocardiogram; CAT Scan; chest x-ray; ultrasound such as Doppler ultrasound; anti-coagulation level test; average clotting time test; pulmonary capillary wedge pressure (PCWP) test; pulmonary artery pressure (PAP) test; hemolysis test such as a plasma free hemoglobin test; cardiac output test; stress test such as a patient positional stress test; and combinations of these.

While the flow systems of the present inventive concepts have been described in detail as circulating blood, other fluids such as other body fluids can be circulated by the system.

While the preferred embodiments of the systems, methods and devices have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. The various aspects and features of this disclosure may be combined in any desired manner. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A blood flow system for a patient comprising:
   a fluid drive module comprising:
      a housing defining a chamber;
      an inlet port, the inlet port being adapted to be in fluid communication with the chamber;
      an outlet port, the outlet port being adapted to be in fluid communication with the chamber;
      a rotatable fluid drive element within the chamber, the fluid drive element configured to move the fluid; and
      a motor connected to the fluid drive element, the motor being configured to rotate the fluid drive element;
   a control module operably coupled to the motor, the control module configured to operate the fluid drive module by controlling a rotational speed of the fluid drive element and to collect quantitative and/or qualitative flow data when the fluid drive element is being operated; and
   wherein the control module is configured to average the data over a first time interval and a second time interval, compare the averaged data from the first and second time intervals to produce a result, compare the result to a threshold, and, if the comparison of the result to the threshold is unacceptable, perform a modification of the speed of the fluid drive element.

2. A method for operating a blood flow system for a patient, the system comprising a fluid drive module, the fluid drive module comprising a housing defining a chamber, an inlet port, an outlet port, a rotatable fluid drive element within the chamber, and a motor connected to the fluid drive element, and a control module configured to operate the fluid drive module, the method comprising:

operating the fluid drive element in a continuous series of changing speeds, wherein the continuous series of changing speeds includes repeated sets of speeds.

3. The method of claim 2, wherein operating the fluid drive element in a continuous series of changing speeds includes:

operating the fluid drive element at a first speed for a first time period, the first speed generating a first speed flow pattern comprising one or more first speed flow parameters; and operating the fluid drive element at a second speed for a second time period, wherein the second speed is constructed and arranged to modify one or more of the first speed flow parameters.

4. The method of claim 3, wherein operating the fluid drive element in a continuous series of changing speeds includes:

operating the fluid drive element at a third speed for a third time period, wherein the third speed is constructed and arranged to modify one or more of the first speed flow parameters.

5. A method for operating a blood flow system for a patient, the system comprising a fluid drive module, the fluid drive module comprising a housing defining a chamber, an inlet port, an outlet port, a rotatable fluid drive element within the chamber, and a motor connected to the fluid drive element, and a control module configured to operate the fluid drive module, the method comprising:

operating the fluid drive element at a first speed for a first time period, the first speed generating a first speed flow pattern comprising one or more first speed flow parameters;

collecting quantitative and/or qualitative flow data;

performing an analysis of the one or more first speed flow parameters; and modifying the speed of the fluid drive element based on the analysis, wherein modifying the speed includes:

averaging the data over a first time interval and a second time interval;

comparing the averaged data from the first and second time intervals to produce a result;

comparing the result to a threshold; and if the comparison of the result to the threshold is unacceptable, modifying the speed of the fluid drive element.

* * * * *